US006743774B1

(12) United States Patent
Jay

(10) Patent No.: US 6,743,774 B1
(45) Date of Patent: Jun. 1, 2004

(54) TRIBONECTINS

(75) Inventor: Gregory D. Jay, Norfolk, MA (US)

(73) Assignee: Rhode Island Hospital, Providence, RI (US)

( * ) Notice: Subject to any disclaimer, the term of this patent is extended or adjusted under 35 U.S.C. 154(b) by 0 days.

(21) Appl. No.: 09/298,970

(22) Filed: Apr. 23, 1999

(51) Int. Cl.$^7$ .................. A01N 37/18; A61K 38/00; A61K 38/16; C07K 14/00; C07K 17/00

(52) U.S. Cl. .................. 514/8; 514/2; 514/21; 530/350

(58) Field of Search .................. 514/2, 21, 8; 530/300, 530/350

(56) References Cited

U.S. PATENT DOCUMENTS

| | | | |
|---|---|---|---|
| 2,487,377 A | 11/1949 | Roechner et al. | 252/42.11 |
| 2,734,862 A | 2/1956 | Morway et al. | 252/14 |
| 2,878,184 A | 3/1959 | March et al. | 252/15 |
| 4,108,849 A | 8/1978 | Thomas | 260/122 |
| 4,438,100 A | 3/1984 | Balslev et al. | 424/104 |
| 5,260,417 A | 11/1993 | Grant et al. | 430/351 |
| 5,326,558 A | 7/1994 | Turner et al. | 424/85.1 |
| 5,403,592 A * | 4/1995 | Hills | 424/450 |
| 5,510,121 A | 4/1996 | Rhee et al. | 424/520 |
| 5,510,122 A | 4/1996 | Sreebny et al. | 424/537 |
| 5,515,590 A | 5/1996 | Pienkowswki | 29/404 |
| 5,605,938 A * | 2/1997 | Roufa et al. | 514/59 |
| 5,612,028 A | 3/1997 | Sackier et al. | 424/93.7 |
| 5,639,796 A | 6/1997 | Lee | 514/773 |
| 5,702,456 A | 12/1997 | Pienkowski | 623/18 |
| 5,709,020 A | 1/1998 | Pienkowski et al. | 427/2.26 |

OTHER PUBLICATIONS

Aydelotte et al. (1992) "Heterogeneity of Articular Chondrocytes", *Articular Cartilage and Osteoarthritis*, Raven Press Ltd., New York, pp. 237–249.

J.P. Caron (1992) "Understanding the Pathogenesis of Equine Osteoarthritis", *Br. VetJSci.* USA, vol. 149, pp. 369–371.

Flannery et al. (1999) "Articular Cartilage Superficial Zone Protein (SZP) is Homologous to Megakaryocyte Stimulating Factor Precursor and is a Mutifunctional Proteoglycan with Potential Growth–Promoting, Cytoprotective, anmd Lubricating Properties in Cartilage Metabolism", *Biochemical and Biophysical Communications*, vol. 254, pp. 535–541.

Garg et al (1979) "The Structure of the O–Glycosylically–linked Oligosacharide Chains of LPG–I, A Glycoprotein Present in Articular Lubricating Fraction of Bovine Synovial Fluid" *Carbohydrate Research*, vol. 78, pp. 79–88.

Jay (1992) "Characterization of a Bovine Synovial Fluid Lubricating Factor. I. Chemical, Surface Activity and Lubricating Properties" *Connective Tissue Research*, vol. 28, pp. 71–88.

Jay et al. (1992) "Characterization of a Bovine Synovial Fluid Lubricating Factor. II. Comparison with Purified Ocular and Salivary Mucin" *Connective Tissue Research*, vol. 28, pp. 89–98.

Jay et al. (1992) "Characterization of a Bovine Synovial Fluid Lubricating Factor. III. The Interaction with Hyaluronic Acid" *Connective Tissue Research*, vol. 28, pp. 245–255.

Jay et al. (1990), "Silver Staining of Extensively Glycosylated Proteins on Sodium Dodecyl Sulfate–Polyacrylamide Gels: Enhancement by Carbohydrate–Binding Dyes", *Analytical Biochenistry*, vol. 185, pp. 324–330.

Jay et al. (1998) "Comparison of the Boundary–Lubricating Ability of Bovine Synovial Fluid, Lubricin, and Healon", J Biomed Mater Res, vol. 40, pp. 414–418.

Jay (1990), "Joint Lubrication: A Physicochemical Study of a Purified Lubrication Factor from Bovine Synovial Fluid", Thesis, Degree of Doctor of Philosophy, Basis Health Sciences (Cellular and Molecular Pathology), State University of New York.

Lorenzo et al. (1998) "A Novel Catilage Protein (CILP) Present in the Mid–zone of Human Articular Cartilage Increases with Age", *J. of Biological Chemistry*, vol. 273, No. 36, pp. 23463–23468.

Lorenzo et al. (1998) "Cloning and Deduced Amino Acid Sequence of a Novel Cartilage Protein (CILP) Identifies a Profrom Including a Nucleotide Pyrophosphohydrolase", *J of Biological Chemistry*, vol. 273, No. 36, pp. 23469–23475.

Merberg et al. (1993) "A Comparison of Vitronectin and Megakaryocyte Stimulating Factor", Elsevier Science Publishers, B.V., pp. 45–53.

Schumacher et al. (1999) "Immunodetection and Partial cDNA Sequence of the Proteoglycan, Superficial Zone Protein, Synthesized by Cells Lining Synovial Joints", *J Orthopaedic Research*, vol. 17, pp. 110–121.

Schumacher et al. (1994) "A Novel Proteoglycan Synthesized and Secreted by Chondrocytes of the Superficial Zone of Articular Cartilage", *Archives of Biochemistry and Biophysics*, vol. 311, pp. 144–152.

Swann et al. (1985) "The Molecular Structure and Lubricating Activity of Lubricin Isolated from Bovine and Human Synovial Fluids", *Biochem J*, vol. 225, pp. 195–201.

Swann et al. (1981) "The Molecular Structure of Lubricating Glycoprotein–I, the Boundary Lubricant for Articular Cartilage", *J. Biological Chemistry*, vol. 256, No. 11, pp. 5921–5925.

(List continued on next page.)

Primary Examiner—Anne-Marie Falk
(74) Attorney, Agent, or Firm—Ingrid A. Beattie; Mintz, Levin, Cohn, Ferris, Glovsky, and Popeo, P.C.

(57) ABSTRACT

The invention features a tribonectin and a method of tribosupplementation carried out by administering tribonectins directly to an injured or arthritic joint.

26 Claims, No Drawings-

OTHER PUBLICATIONS

Turner et al. (1991) "Purification, Biochemical Characterization, and Cloning of a Novel Megakaryocyte Stimulating Factor that has Megakaryocyte Colony Stimulating Activity", Blood, vol. 78 (Suppl. 1), pp. 279.

Schumacher et al., 1999, "Immunodetection and Partial cDNA Sequence of the Proteoglycan, Superficial Zone Protein Synthesized by Cells Lining Synovial Joints", Journal of Orthopaedic Research, 17:110–120.

* cited by examiner

TRIBONECTINS

BACKGROUND OF THE INVENTION

The invention relates to lubrication of mammalian joints.

Osteoarthritis (OA) is the one of the most common form of joint disease. Factors which contribute to the development of OA include a family history of OA, previous damage to the joint through injury or surgery, and age of the joint, i.e., "wear and tear" of the articulating surfaces of the joint. OA is very common in older age groups, but can affect children as well.

Current treatment is directed to relieving pain and other symptoms of OA, e.g., by administering analgesics and anti-inflammatory drugs. Other therapeutic approaches include viscosupplementation by administering hyaluronic acid and derivatives thereof to joint tissue to increase the viscosity of synovial fluid.

SUMMARY OF THE INVENTION

The invention features a novel treatment for osteoarthritis and other degenerative joint diseases by tribosupplementation. Tribosupplementation is carried out by administering lubricating polypeptides directly to the injured or arthritic joint. Unlike viscosupplementation, tribosupplementation does not substantially increase the viscosity of the solution, e.g, synovial fluid, to which it is added. The viscosity of a solution to which a tribonectin is added increases no more than 10%, preferably no more than 5%, more preferably no more than 2%, more preferably no more than 1%. Most preferably, the viscosity of the solution to which a tribonectin is added is unaltered or decreases.

Accordingly, the invention provides a tribonectin. A tribonectin is an artificial boundary lubricant which contains at least one repeat of an amino acid sequence which is at least 50% identical to KEPAPTT (SEQ ID NO:3). A tribonectin is formulated for administration to a mammalian joint. Preferably, the tribonectin is a recombinant or chemically-synthesized lubricating polypeptide. For example, a tribonectin includes a substantially pure polypeptide the amino acid sequence of which includes at least one but less than 76 subunits. Each subunit contains at least 7 amino acids (and typically 10 or fewer amino acids). The amino acid sequence of each subunit is at least 50% identical to SEQ ID NO:3, and a non-identical amino acid in the reference sequence is a conservative amino acid substitution. For example, one or both of the threonine residues are substituted with a serine residue. Preferably, the amino acid sequence of the subunit is identical to SEQ ID NO:3. The tribonectin may also contain one or more repeats of the amino acid sequence XXTTTX (SEQ ID NO:4). Polypeptides or other compounds described herein are said to be "substantially pure" when they are within preparations that are at least 60% by weight (dry weight) the compound of interest. Preferably, the preparation is at least 75%, more preferably at least 90%, and most preferably at least 99%, by weight the compound of interest. Purity can be measured by any appropriate standard method, for example, by column chromatography, polyacrylaminde gel electrophoresis, or HPLC analysis.

Where a particular polypeptide or nucleic acid molecule is said to have a specific percent identity to a reference polypeptide or nucleic acid molecule of a defined length, the percent identity is relative to the reference polypeptide or nucleic acid molecule. Thus, a peptide that is 50% identical to a reference polypeptide that is 100 amino acids long can be a 50 amino acid polypeptide that is completely identical to a 50 amino acid long portion of the reference polypeptide. It can also be a 100 amino acid long polypeptide which is 50% identical to the reference polypeptide over its entire length.

A polypeptide or nucleic acid molecule which is "substantially identical" to a given reference polypeptide or nucleic acid molecule is a polypeptide or nucleic acid molecule having a sequence that has at least 85%, preferably 90%, and more preferably 95%, 98%, 99% or more identity to the sequence of the given reference polypeptide sequence or nucleic acid molecule. "Identity" has an art-recognized meaning and is calculated using well known published techniques, e.g., Computational Molecular Biology, 1988, Lesk A. M., ed., Oxford University Press, New York; Biocomputing: Informatics and Genome Projects, 1993, Smith, D. W., ed., Academic Press, New York; Computer Analysis of Sequence Data, Part I, 1994, Griffin, A. M. and Griffin, H. G., eds., Humana Press, New Jersey; Sequence Analysis in Molecular Biology, 1987, Heinje, G., Academic Press, New York; and Sequence Analysis Primer, 1991, Gribskov, M. and Devereux, J., eds., Stockton Press, New York). While there exist a number of methods to measure identity between two polynucleotide or polypeptide sequences, the term "identity" is well known to skilled artisans and has a definite meaning with respect to a given specified method. Sequence identity described herein is measured using the Sequence Analysis Software Package of the Genetics Computer Group (GCS), University of Wisconsin Biotechnology Center, 1710 University Avenue, Madison, Wis. 53705), with the default parameters as specified therein.

A tribonectin is characterized as reducing the coefficient of friction ($\mu$) between bearing surfaces. For example, reduction of friction is measured in vitro by detecting a reduction in friction in a friction apparatus using latex:glass bearings. Reduction of friction is also measured in vivo, e.g., by measuring reduction of patient pain. Tribonectins of the invention are lubricating compositions. Polypeptides that have at least 50% (but less than 100%) amino acid sequence identity to a reference sequence are tested for lubricating function by measuring a reduction in the $\mu$ between bearing surfaces.

A tribonectin includes an O-linked oligosaccharide, e.g., an N-acetylgalactosamine and galactose in the form $\beta(1–3)$ Gal-GalNAC. For example, KEPAPTT (SEQ ID NO:3) and XXTTTX (SEQ ID NO:4) repeat domains are glycosylated by $\beta(1–3)$Gal-GalNAC (which may at times be capped with NeuAc in the form of $\beta(1–3)$Gal-GalNAC-NeuAc. The term "glycosylated" with respect to a polypeptide means that a carbohydrate moiety is present at one or more sites of the polypeptide molecule. For example, at least 10%, preferably at least 20%, more preferably at least 30%, and most preferably at least 40% of the tribonectin is glycosylated. Up to 50% or more of the tribonectin can be glycosylated. Per cent glycosylation is determined by weight.

A tribonectin polypeptide can contain a substantially pure fragment of megakaryocyte stimulating factor (MSF). For example, the molecular weight of a substantially pure tribonectin having an amino acid sequence of a naturally-occurring tribonectin is in the range of 220–280 kDa. Preferably, the apparent molecular weight of a tribonectin is less than 230 kDa, more preferably less than 250 kDa, and most preferably less than 280 kDa. A protein or polypeptide fragment is defined as a polypeptide which has an amino acid sequence that is identical to part, but not all, of the amino acid sequence of a naturally-occurring protein or polypeptide from which it is derived, e.g., MSF. The tribonectin may contain a polypeptide, the amino acid sequence of which is at least 50% identical to the sequence of residues 200–1140, inclusive, of SEQ ID NO:1, e.g., it contains the amino acid sequence of residues 200–1140, inclusive, of SEQ ID NO:1. In another example, the polypeptide contains an amino acid sequence that is at least 50% identical to the sequence of residues 200–1167, inclusive, of SEQ ID NO:1, e.g., one having the amino acid sequence identical to residues 200–1167, inclusive, of SEQ ID NO:1. The polypeptide contains an amino acid sequence that is at least 50% identical to the sequence of residues 200–1212, inclusive, of SEQ ID NO:1, e.g., the amino acid sequence of residues 200–1212, inclusive, of SEQ ID NO:1, or the polypeptide contains an amino acid sequence that is at least 50% identical to the sequence of residues 200–1263, inclusive, of SEQ ID NO:1, e.g., an amino acid sequence identical to residues 200–1263, inclusive, of SEQ ID NO:1. Preferably, the sequence of the polypeptide lacks the amino acid sequence of residues 1–24, inclusive, of SEQ ID NO:1 and/or the amino acid sequence of residues 67–104, inclusive of SEQ ID NO:1.

The invention also features an isolated nucleic acid molecule encoding a tribonectin. For example, the nucleic acid includes a sequence that is at least 50% identical to nucleotides 631–3453, inclusive, of SEQ ID NO:2. Preferably, the nucleic acid encodes a polypeptide with the amino acid sequence of residues 200–1140 of SEQ ID NO:1. For example, the nucleic acid has a nucleotide sequence identical to that of nucleotides 631–3453, inclusive, of SEQ ID NO:2, or a degenerate variant thereof. An isolated nucleic acid molecule is a nucleic acid molecule that is separated from the 5' and 3' coding sequences or non-coding sequences with which it is immediately contiguous in the naturally occurring genome of an organism. Isolated nucleic acid molecules include nucleic acid molecules which are not naturally occurring, e.g., nucleic acid molecules created by recombinant DNA techniques. For example, the nucleic acid of the invention includes nucleotides 631–3453, inclusive, of SEQ ID NO:2, but not nucleotides which are immediately contiguous to those sequences in the naturally-occurring genomic sequence or naturally-occurring cDNA.

Also within the invention is a method of lubricating a mammalian joint by contacting the joint with a tribonectin. The mammal is preferably a human, horse, dog, ox, donkey, mouse, rat, guinea pig, cow, sheep, pig, rabbit, monkey, or cat, and the joint is an articulating joint such as a knee, elbow, shoulder, hip, or any other weight-bearing joint. Tribonectins are administered intra-articularly. Therapeutic joint lubrication is also carried out by gene therapy, e.g., by contacting the joint or synovial fluid with a nucleic acid encoding a tribonectin. For example, nucleic acids are administered to a synovial cavity by intra-articular injection.

In addition to functioning as a boundary lubricant in a mammalian joint, a tribonectin is used as a boundary lubricant between soft mammalian tissues such as skin or internal organs or between a mammalian tissue and a medical device such as a prosthetic implant. Accordingly, the invention encompasses a biocompatible composition containing a tribonectin in a form suitable for the inhibition of tissue adhesion formation. For example, the tribonectin is in the form of a film, membrane, foam, gel, or fiber. The term "film," as used herein, means a substance formed by compressing a foam or gel to a thin membrane, e.g., by casting into a flat mold and air drying to a thin membrane, or by compressing a gel or fibers, or by allowing or causing a gel or fibers to dehydrate. The term "foam," as used herein, means a substance with a porous structure formed, e.g., by introduction of as air into a tribonectin solution, suspension, gels, or fiber. The term "bioabsorbable," as used herein, refers to the ability of a tissue-compatible material to degrade in the body after implantation, into nontoxic products which are eliminated from the body or metabolized. A "biocompatible" substance, as the term is used herein, is one that has no medically unacceptable toxic or injurious effects on biological function. Tribonectin compositions for the prevention of adhesions are also formulated as compositions suitable for extrusion, e.g., to form a mold upon which tissue can grow without adhering.

A method inhibiting adhesion formation between a first surface and a second surface in a mammal is carried out by placing a tribonectin between the first and second surfaces in an amount sufficient to prevent adhesion of the surfaces in the mammal. For example, one or both of the surfaces is a mammalian tissue, and a tribonectin placed between them prevents formation of adhesions during the healing process. Alternatively the first or the second surface (or both) is an artificial device such as an orthopedic implant. Tissues to be treated include those injured by surgical incision or trauma.

Also within the invention is a method for diagnosing osteoarthritis or a predisposition thereto by obtaining a biological sample from a mammal and measuring the amount of an MSF fragment in the biological sample. An increase in the amount compared to a control, e.g, a predetermined value associated with a negative diagnosis or a biological sample from a mammal known to be free of osteoarthritis, indicates that the mammal suffers from osteoarthritis or is predisposed to developing osteoarthritis. Any biological sample is suitable for testing in the diagnostic method; typically, the biological sample is synovial fluid, blood, serum, or urine. Preferably, the MSF fragment contains the amino acid sequence of SEQ ID NO:3. Alternatively, the MSF fragment contains the amino acid sequence of EPAPTT (SEQ ID NO:5; a product of trypsin cleavage of a tribonectin) or the amino acid sequence of PTTKEP (SEQ ID NO:6; a product of elastase cleavage of a tribonectin).

Other features and advantages of the invention will be apparent from the following description of the preferred embodiments thereof, and from the claims.

DETAILED DESCRIPTION

A human lubricating polypeptide was purified from synovial fluid and found to contain amino acids encoded by exons 2 and 4–12 of the MSF gene (but not exons 1 or 3). The gene encoding naturally-occurring full length MSF contains 12 exons, and the naturally-occurring MSF gene product contains 1404 amino acids with multiple polypeptide sequence homologies to vitronectin including hemopexin-like and somatomedin-like regions. Centrally-located exon 6 contains 940 residues. Exon 6 encodes a O-glycosylated mucin domain. A polypeptide encoded by nucleotides 631–3453 of SEQ ID NO:2 provides boundary lubrication of articular Cartilage.

TABLE 1

MSF amino acid sequence

MAWKTLPIYLLLLLSVFVIQQVSSQDLSSCAGRCGEGYSRDATCNCDYNCQHYMECCPDF
KRVCTAELSCKGRCFESFERGRECDCDAQCKKYDKCCPDYESFCAEVHNPTSPPSSKKAP
PPSGASQTIKSTTKRSPKPPNKKKTKKVIESEEITEEHSVSENQESSSSSSSSSSSSTIW
KIKSSKNSAANRELQKKLK<u>VKDNKKNRTKKKPTPKPPVVDEAGSGLDNGDFKVTTPDTST
TQHNKVSTSPKITTAKPINPRPSLPPNSDTSKETSLTVNKETTVETKETTTTNKQTSTDG
KEKTTSAKETQSIEKTSAKDLAPTSKVLAKPTPKAETTTKGPALTTPKEPTPTTPKEPAS
TTPKEPTPTTIKSAPTTPKEPAPTTTKSAPTTPKEPAPTTTKEPAPTTPKEPAPTTTKEP
APTTTKSAPTTPKEPAPTTPKKPAPTTPKEPAPTTPKEPTPTTPKEPAPTTKEPAPTTPK
EPAPTAPKKPAPTTPKEPAPTTPKEPAPTTTKEPSPTTPKEPAPTTTKSAPTTTKEPAPT
TTKSAPTTPKEPSPTTTKEPAPTTPKEPAPTTPKKPAPTTPKEPAPTTPKEPAPTTTKKP
APTAPKEPAPTTPKETAPTTPKKLTPTTPEKLAPTTPEKPAPTTPEELAPTTPEEPTPTT
PEEPAPTTPKAAAPNTPKEPAPTTPKEPAPTTPKEPAPTTPKETAPTTPKGTAPTTLKEP
APTTPKKPAPKELAPTTTKEPTSTTSDKPAPTTPKGTAPTTPKEPAPTTPKEPAPTTPKG
TAPTTLKEPAPTTPKKPAPKELAPTTTKGPTSTTSDKPAPTTPKETAPTTPKEPAPTTPK
KPAPTTPETPPPTTSEVSTPTTTKEPTTIHKSPDESTPELSAEPTPKALENSPKEPGVPT
TKTPAATKPEMTTTAKDKTTERDLRTTPETTTAAPKMTKETATTTEKTTESKITATTTQV
TSTTTQDTTPFKITTLKTTTLAPKVTTTKKTITTTEIMNKPEETAKPKDRATNSKATTPK
PQKPTKAPKKPTSTKKPKTMPRVRKPKTTPTPRKMTSTMPELNPTSRIAEAMLQTTTRPN
QTPNSKLVEVNPKSEDAGGAEGETPHMLLRPHVFMPEVTPDMDYLPRVPNQGIIINPMLS</u>
DETNICNGKPVDGLTTLRNGTLVAFRGHYFWMLSPFSPPSPARRITEVWGIPSPIDTVFT
RCNCEGKTFFFKDSQYWRFTNDIKDAGYPKPIFKGFGGLTGQIVAALSTAKYKNWPESVY
FFKRGGSIQQYIYKQEPVQKCPGRRPALNYPVYGEMTQVRRRRFERAIGPSQTHTIRIQY
SPARLAYQDKGVLHNEVKVSILWRGLPNVVTSAISLPNIRKPDGYDYYAFSKDQYYNIDV
PSRTARAITTRSGQTLSKVWYNCP (SEQ ID NO:1)

TABLE 2

MSF cDNA

```
  1 gcggccgcga ctattcggta cctgaaaaca acgatggcat ggaaaacact tcccatttac
 61 ctgttgttgc tgctgtctgt tttcgtgatt cagcaagttt catctcaaga tttatcaagc
121 tgtgcaggga gatgtgggga agggtattct agagatgcca cctgcaactg tgattataac
181 tgtcaacact acatggagtg ctgccctgat ttcaagagag tctgcactgc ggagctttcc
241 tgtaaaggcc gctgctttga gtccttcgag agagggaggg agtgtgactg cgacgcccaa
301 tgtaagaagt atgacaagtg ctgtcccgat tatgagagtt tctgtgcaga agtgcataat
361 cccacatcac caccatcttc aaagaaagca cctccacctt caggagcatc tcaaaccatc
421 aaatcaacaa ccaaacgttc acccaaacca ccaaacaaga agaagactaa gaaagttata
481 gaatcagagg aaataacaga gaacattct gtttctgaaa atcaagagtc ctcctcctcc
541 tcctcctctt cctcttcttc ttcaacaatt tggaaaatca gtcttccaa aaattcagct
                                    EXON 6
601 gctaatagag aattacagaa gaaactcaaa gtaaaagata caagaagaa cagaactaaa
```

TABLE 2-continued

MSF cDNA

```
 661 aagaaaccta cccccaaacc accagttgta gatgaagctg gaagtggatt ggacaatggt
 721 gacttcaagg tcacaactcc tgacacgtct accacccaac acaataaagt cagcacatct
 781 cccaagatca aacagcaaa accaataaat cccagaccca gtcttccacc taattctgat
 841 acatctaaag agacgtcttt gacagtgaat aaagagacaa cagttgaaac taagaaact
 901 actacaacaa ataaacagac ttcaactgat ggaaaagaga agactacttc cgctaaagag
 961 acacaaagta tagagaaaac atctgctaaa gatttagcac ccacatctaa agtgctggct
1021 aaacctacac ccaaagctga aactacaacc aaaggccctg ctctcaccac tcccaaggag
1081 cccacgccca ccactcccaa ggagcctgca tctaccacac ccaaagagcc cacacctacc
1141 accatcaagt ctgcacccac caccccaag gagcctgcac ccaccaccac caagtctgca
1201 cccaccactc ccaaggagcc tgcacccacc accaccaagg agcctgcacc caccactccc
1261 aaggagcctg cacccaccac caccaaggag cctgcaccca ccaccaagtc tgcacccacc
1321 accactccca aggagcctgc acccaccacc ccaagaagc tgccccaac tacccccaag
1381 gagcctgcac ccaccactcc caaggagcct acacccacca ctcccaagga gcctgcaccc
1441 accaccaagg agcctgcacc caccactccc aaagagcctg cacccactgc ccccaagaag
1501 cctgccccaa ctaccccaa ggagcctgca cccaccactc caaggagcc tgcacccacc
1561 accaccaagg agccttcacc caccactccc aaggagcctg cacccaccac caccaagtct
1621 gcacccacca ctaccaagga gcctgcaccc accactacca agtctgcacc caccactccc
1681 aaggagcctt cacccaccac caccaaggag cctgcaccca ccactcccaa ggagcctgca
1741 cccaccaccc caagaagcc tgccccaact accccaagg agcctgcacc caccactccc
1801 aaggaacctg cacccaccac caccaagaag cctgcaccca ccgctcccaa agagcctgcc
1861 ccaactaccc ccaaggagac tgcacccacc accccaaga agctcacgcc caccaccccc
1921 gagaagctcg cacccaccac ccctgagaag cccgcaccca ccaccctga ggagctcgca
1981 cccaccaccc ctgaggagcc cacacccacc acccctgagg agcctgctcc caccactccc
2041 aaggcagcgg ctcccaacac ccctaaggag cctgctccaa ctacccctaa ggagcctgct
2101 ccaactaccc ctaaggagcc tgctccaact acccctaagg agactgctcc aactacccct
2161 aaagggactg ctccaactac cctcaaggaa cctgcaccca ctactcccaa gaagcctgcc
2221 cccaaggagc ttgcacccac caccaccaag gagcccacat ccaccacctc tgacaagccc
2281 gctccaacta cccctaaggg gactgctcca actacccta aggagcctgc tccaactacc
2341 cctaaggagc ctgctccaac taccctaag gggactgctc caactaccct caaggaacct
2401 gcacccacta ctcccaagaa gcctgccccc aaggagcttg cacccaccac caagggg
2461 cccacatcca ccacctctga caagcctgct ccaactacac ctaaggagac tgctccaact
2521 accccaagg agcctgcacc cactacccc aagaagcctg ctccaactac tcctgagaca
2581 cctcctccaa ccacttcaga ggtctctact ccaactacca ccaaggagcc taccactatc
2641 cacaaaagcc ctgatgaatc aactcctgag ctttctgcag aacccacacc aaaagctctt
2701 gaaaacagtc ccaggaacc tggtgtacct acaactaaga ctcctgcagc gactaaacct
2761 gaaatgacta acacagctaa agacaagaca acagaaagag acttacgtac tacacctgaa
2821 actacaactg ctgcacctaa gatgacaaaa gagacagcaa ctacaacaga aaaaactacc
2881 gaatccaaaa taacagctac aaccacacaa gtaacatcta ccacaactca agataccaca
```

TABLE 2-continued

MSF cDNA 2941 ccattcaaaa ttactactct taaaacaact actcttgcac ccaaagtaac tacaacaaaa 3001 aagacaatta ctaccactga gattatgaac aaacctgaag aaacagctaa accaaaagac 3061 agagctacta attctaaagc gacaactcct aaacctcaaa agccaaccaa agcacccaaa 3121 aaacccactt ctaccaaaaa gccaaaaaca atgcctagag tgagaaaacc aaagacgaca 3181 ccaactcccc gcaagatgac atcaacaatg ccagaattga accctacctc aagaatagca 3241 gaagccatgc tccaaaccac caccagacct aaccaaactc caaactccaa actagttgaa 3301 gtaaatccaa agagtgaaga tgcaggtggt gctgaaggag aaacacctca tatgcttctc 3361 aggcccatg tgttcatgcc tgaagttact cccgacatgg attacttacc gagagtaccc 3421 aatcaaggca ttatcatcaa tcccatgctt tccgatgaga ccaatatatg caatggtaag 3481 ccagtagatg gactgactac tttgcgcaat gggacattag ttgcattccg aggtcattat 3541 ttctggatgc taagtccatt cagtccacca tctccagctc gcagaattac tgaagtttgg 3601 ggtattcctt cccccattga tactgttttt actaggtgca actgtgaagg aaaaactttc 3661 ttctttaagg attctcagta ctggcgtttt accaatgata taaaagatgc agggtacccc 3721 aaaccaattt tcaaaggatt tggaggacta actggacaaa tagtggcagc gctttcaaca 3781 gctaaatata agaactggcc tgaatctgtg tattttttca agagagtgg cagcattcag 3841 cagtatattt ataaacagga acctgtacag aagtgccctg gaagaaggcc tgctctaaat 3901 tatccagtgt atggagaaat gacacaggtt aggagacgtc gctttgaacg tgctatagga 3961 ccttctcaaa cacacaccat cagaattcaa tattcacctg ccagactggc ttatcaagac 4021 aaaggtgtcc ttcataatga agttaaagtg agtatactgt ggagaggact tccaaatgtg 4081 gttacctcag ctatatcact gcccaacatc agaaaacctg acggctatga ttactatgcc 4141 ttttctaaag atcaatacta taacattgat gtgcctagta aacagcaag agcaattact 4201 actcgttctg ggcagacctt atccaaagtc tggtacaact gtccttagac tgatgagcaa 4261 aggaggagtc aactaatgaa gaaatgaata ataaattttg acactgaaaa acattttatt 4321 aataaagaat attgcacatga gtataccagt ttatatataa aaatgttttt aaacttgaca 4381 atcattacac taaaacagat ttgataatct tattcacagt tgttattgtt tacagaccat 4441 ttaattaata tttcctctgt ttattcctcc tctccctccc attgcatggc tcacacctgt 4501 aaaagaaaaa agaatcaaat tgaatatatc ttttaagaat tcaaaactag tgtattcact 4561 taccctagtt cattataaaa aatatctagg cattgtggat ataaaactgt tgggtattct 4621 acaacttcaa tggaaattat tacaagcaga ttaatccctc ttttttgtgac acaagtacaa 4681 tctaaaagtt atattggaaa acatggaaat attaaaattt tacacttttta ctagctaaaa 4741 cataatcaca aagctttatc gtgttgtata aaaaaattaa caatataatg gcaataggta 4801 gagatacaac aaatgaatat aacactataa cacttcatat tttccaaatc ttaatttgga 4861 tttaaggaag aaatcaataa atataaaata taagcacata tttattatat atctaaggta 4921 tacaaatctg tctacatgaa gtttacagat tggtaaatat cacctgctca acatgtaatt 4981 atttaataaa actttggaac attaaaaaaa taaattggag gcttaaaaaa aaaaaaaaa 5041 a (SEQ ID NO:2)

TABLE 3

MSF Exon Boundaries

| Exon | Amino acid sequence in SEQ ID NO:1 | Nucleotide sequence in SEQ ID NO:2 |
|---|---|---|
| 1 | 1–24, inclusive | 34–105, inclusive |
| 2 | 25–66, inclusive | 106–231, inclusive |
| 3 | 67–104, inclusive | 232–345, inclusive |
| 4 | 105–155, inclusive | 346–498, inclusive |
| 5 | 156–199, inclusive | 499–630, inclusive |
| 6 | 200–1140, inclusive | 631–3453, inclusive |
| 7 | 1141–1167, inclusive | 3454–3534, inclusive |
| 8 | 1168–1212, inclusive | 3535–3670, inclusive |
| 9 | 1213–1263, inclusive | 3671–3822, inclusive |
| 10 | 1264–1331, inclusive | 3823–4026, inclusive |
| 11 | 1332–1371, inclusive | 4027–4146, inclusive |
| 12 | 1372–1404, inclusive | 4147–4245, inclusive |

The boundary lubricant isolated from synovial fluid is an alternatively-spliced variant of MSF. This alternatively-spliced variant was found to be the composition present in synovial fluid that confers lubricating capabilities to the articular joint. The boundary lubricant isolated from human synovial fluid contains amino acids encoded by exons 2, and 4–12 of the MSF gene, i.e., the alternative splice variant lacks amino acids encoded by exons 1 and 3 of the MSF gene. A recombinant or chemically-produced polypeptide containing at least exon 6 (but not exons 1 or 3) of MSF is useful to prevent and/or treat osteoarthritic disease. A recombinant or chemically-produced lubricating polypeptide containing at least one repeat of the amino acid sequence KEPAPTT (SEQ ID NO:3) either identically or with conservative substitution is also administered to lubricate mammalian joints.

Production and Purification of Recombinant Lubricating Polypeptides

To produce recombinant polypeptides, DNA containing exon 6 of MSF (nucleotides 631–3453 of SEQ ID NO:2) in an appropriate expression vector is transfected into a cell. The DNA can also contain some or all of exon 7 (nucleotides 354–3534 of SEQ ID NO:2), exon 8 (nucleotides 3535–3670 of SEQ ID NO:2), or exon 9 (nucleotides 3671–3822 of SEQ ID NO:2) of the MSF gene. Primers for polymerase chain reaction (PCR) methods to generate DNA which spans various exons of MSF are shown below.

TABLE 4

PCR Primers

| MSF exons | Forward Primer | Reverse Primer |
|---|---|---|
| exon 2 | 5'AGATTTATCAAGCTGT GCAGGGAG3' (SEQ ID NO:7) | 5'TTTACAGGAAAGC TCCGCAGTG3' (SEQ ID NO:8) |
| exon 6 | 5'TCAAGGTCACAACTCC TGACACG3' (SEQ ID NO:9) | 5'CTCTCGGTAAGTA ATCCATGTCGG3' (SEQ ID NO:10) |
| exons 2–12 | 5'TTGTTGCTGCTGTCTG TTTTCG3' (SEQ ID NO:11) | 5'TGGATAAGGTCTG CCCAGAACGAG3' (SEQ ID NO:12) |
| exons 6–12 | 5'TCAAGGTCACAACTCC TGACACG3' (SEQ ID NO: 13) | 5'GATGGTGTGTGTT TGAGAAGGTCC3' (SEQ ID NO:14) |

Methods of designing forward and reverse primers used to make DNAs which encode tribonectin polypeptides of varying lengths and which incorporate various exons of the MSF gene, e.g., to make polypeptide encoded by exons 2, 4–12; exons 6–9; and exons 2, 4–9, are well known in the art of molecular biology. Standard methods for transfecting cells with isolated nucleic acid are well known to those skilled in the art of molecular biology. For example, prokaryotic or eukaryotic cells in culture are transfected with the DNA of the invention operatively linked to expression control sequences appropriate for high-level expression in the cell. Such cells are useful for producing large amounts of the lubricating polypeptide, which are purified using standard methods. The lubricating polypeptides are used therapeutically for treatment or prevention of arthritic diseases. The polypeptides are also used to raise antibodies against a naturally-occurring or recombinantly-produced lubricating glycoproteins or glycopeptides.

For example, the recombinant gene product is expressed as a fusion protein and purified using a commercially available expression and purification system, e.g., the PFLAG expression system (IBI). The expression systems that may be used for purposes of the invention include, but are not limited to, microorganisms such as bacteria (e.g., *E. coli* and *B. subtilis*) transformed with recombinant bacteriophage DNA, plasmid DNA, or cosmid DNA expression vectors containing the nucleic acid molecules described herein. For production of glycosylated polypeptides, eukaryotic expression systems are used. Yeast (for example, Saccharomyces and Pichia) transformed with recombinant yeast expression vectors containing the recombinant nucleic acid encoding a tribonectin polypeptide are used. Insect cell systems infected with recombinant virus expression vectors (for example, baculovirus) containing the nucleic acid molecules encoding a tribonectin and mammalian cell systems (e.g., COS, CHO, BHK, 293, VERO, HeLa, MDCK, WI38, and NIH 3T3 cells) harboring recombinant expression constructs containing promoters derived from the genome of mammalian cells (e.g., the metallothionein promoter) or from mammalian viruses (e.g., the adenovirus late promoter and the vaccinia virus 7.5K promoter) are also useful. In addition to clinical applications, recombinant polypeptides are injected into a rabbit or rodent to produce antibodies as described below.

The synovial fluid of an inflamed or injured joint contains proteolytic enzymes that degrade lubricating proteins or polypeptides. For example, infiltrating immune cells such as neutrophils secrete trypsin and/or elastase. Even a minor injury to an articulating joint or an inflammatory state can result in cellular infiltration and proteolytic enzyme secretion resulting in traumatic synovitis. Synovitis for a period of a few days or weeks can result in the loss of the cytoprotective layer of a joint, which in turn leads to the loss of cartilage. Non-lubricated cartilaginous bearings may experience premature wear which may initiate osteoarthritis. Individuals who clinically present with a traumatic effusion (e.g., "water on the knee") are predisposed to developing osteoarthritis; the elaboration of proteolytic enzymes degrades and depletes naturally-occurring lubricating compositions in the synovial fluid. Depletion of natural lubricating compositions occurs in other inflammatory joint diseases such as rheumatoid arthritis. Replacing or supplementing the synovial fluid of such injured joints with the lubricating compositions of the invention prevents the development of osteoarthritis in the long term (e.g., years, even decades later) and immediately lubricates the joint to minimize short term damage.

Analogs, homologs, or mimetics of lubricating peptides which are less susceptible to degradation in vivo are used to lubricate mammalian joints. Analogs can differ from the naturally-occurring peptides by amino acid sequence, or by modifications which do not affect the sequence, or both. Modifications (which do not normally alter primary sequence) include in vivo or in vitro chemical derivitization of polypeptides, e.g., acetylation or carboxylation. Also included are modifications of glycosylation, e.g., those made by modifying the glycosylation patterns of a polypeptide during its synthesis and processing or in further processing steps, e.g., by exposing the polypeptide to enzymes which affect glycosylation, e.g., mammalian glycosylating or deglycosylating enzymes.

Where proteolytic degradation of the peptides following injection into the subject is a problem, replacement of a particularly sensitive peptide bond with a noncleavable peptide mimetic bond renders the resulting peptide more stable, and thus more useful as a therapeutic. To render the therapeutic peptides less susceptible to cleavage by peptidases such as trypsin or elastase, the peptide bonds of a peptide may be replaced with an alternative type of covalent bond (a "peptide mimetic"). Trypsin, elastase, and other enzymes may be elaborated by infiltrating immune cells during joint inflammation. Trypsin cleaves a polypeptide bond on the carboxy-side of lysine and arginine; elastase cleaves on the carboxy-side of alanine, glycine. Thrombin, a serine protease which is present in hemorrhagic joints, cleaves a peptide bond on the carboxy-side of arginine. Collagenases are a family of enzymes produced by fibroblasts and chondrocytes when synovial metabolism is altered (e.g., during injury). These enzymes cut on the carboxy-side of glycine and proline. One or more peptidase-susceptible peptide bonds, e.g, those which appear in the KEPAPTT (SEQ ID NO:3) repeat sequence, are altered (e.g., replaced with a non-peptide bond) to make the site less susceptible to cleavage, thus increasing the clinical half-life of the therapeutic formulation.

Such mimetics, and methods of incorporating them into polypeptides, are well known in the art. Similarly, the replacement of an L-amino acid residue with a D-amino acid is a standard way of rendering the polypeptide less sensitive to proteolysis. Also useful are amino-terminal blocking groups such as t-butyloxycarbonyl, acetyl, theyl, succinyl, methoxysuccinyl, suberyl, adipyl, azelayl, dansyl, benzyloxycarbonyl, fluorenylmethoxycarbonyl, methoxyazelayl, methoxyadipyl, methoxysuberyl, and 2,4-dinitrophenyl.

Clinical formulations of tribonectins may also contain peptidase inhibitors such as N-methoxysuccinyl-Ala-Ala-Pro-Val chloromethylketone (an inhibitor of elastase). Other clinically acceptable protease inhibitors (e.g., as described in Berling et al., 1998, Int. J. Pancreatology 24:9–17) such as leupeptin, aprotinin, α1-antitrypsin, α2-macroglobulin, α1-protease inhibitor, antichymotrypsin (ACHY), secretory leukocyte protease inhibitor (PSTI) are also co-administered with a tribonectin to reduce proteolytic cleavage and increase clinical halflife. A cocktail of two or more protease inhibitors can also be coadministered.

Compositions of tribonectin polypeptides or nucleic acids encoding the polypeptides are formulated in standard physiologically-compatible excipients known in the art., e.g., phosphate-buffered saline (PBS). Other formulations and methods for making-such formulations are well known and can be found in, e.g., "Remington's Pharmaceutical Sciences". Tribonectins are also formulated with non-crosslinked hyaluronic acid preparations or viscosupplementation compositions, such as cross-linked hyaluronic acid preparations. When a tribonectin is added to a viscosupplement formulation, the interaction of the tribonectin with hyaluronic acid reduces the viscosity of the viscosupplement.

Methods of making a glycopeptide and determining % glycosylation are known in the art, e.g., as described in U.S. Pat. No. 5,767,254. The presence of N-acetylgalactosamine is indicative of the presence of O-linked oligosaccharides (or Ser/Thr-linked oligosaccharides) in which GalNAc is commonly found in O-glycosidic alpha-linkage directly to amino acid. The presence of O-linked oligosaccharide is also detected by binding to Jacalin-Sepharose, an immobilized plant lectin that binds to the core disaccharide sequence Gal β(1–3)GalNAc linked to Ser/Thr in glycoproteins, or peanut agglutinin, which binds to β(1–3)Gal-GalNAC. O-linked oligosaccharides are distinguished from N-linked oligosaccharides using standard methods. For example, oligosaccharides in O-glycosidic linkage, but not in N-glycosidic linkage, are susceptible to release from peptide by treatment with mild base in the presence of sodium borohydride (50 mM NaOH, 1M NaBH$_4$, 16 hr at 45° C.) to cause a beta-elimination reaction.

Veterinary Applications

Canine osteoarthritis is a prevalent clinical disorder that is treated using the methods described herein. Osteoarthritis afflicts an estimated one in five adult dogs; an estimated 8 million dogs suffer from this degenerative, potentially debilitating disease. Yet, many owners do not recognize the signs of chronic canine pain. While any dog can develop osteoarthritis, those most at risk are large breeds, geriatric dogs, very active dogs (such as working or sporting animals), and those with inherited joint abnormalities such as hip or elbow dysplasia.

Equine degenerative joint disease such as osteoarthritis is a cause of lameness and impaired performance in horses. As with humans and other mammals, degenerative joint diseases which affect horses are progressive disorders of synovial joints characterized by articular cartilage degeneration and joint effusion. Acute or chronic trauma, overuse, developmental disease, joint instability and old age leads to synovitis, impaired chondrocyte metabolism, and the formation of fissures in the joint cartilage. Destructive enzymes such as trypsin, elastase, stromelysin and hyaluronidase are released into the joint where they degrade synovial fluid and cartilage components, resulting in decreased synovial fluid viscosity, poor lubrication, depressed cartilage metabolism and enhanced wear resulting in pain and cartilage erosion. Current therapeutic approaches include medications for pain relief and anti-inflammatory drugs. The compositions and methods described herein are useful to replenish the lubricating capabilities of the affected joint.

Administration of Therapeutic Polypeptides

Standard methods for delivery of peptides are used. Such methods are well known to those of ordinary skill in the art. For intra-articular administration, tribonectin is delivered to the synovial cavity at a concentration in the range of 20–500 µg/ml in a volume of approximately 0.1–2 ml per injection. For example, 1 ml of a tribonectin at a concentration of 250 µg/ml is injected into a knee joint using a fine (e.g., 14–22 gauge, preferably 18–22 gauge) needle. The compositions of the invention are also useful for parenteral administration, such as intravenous, subcutaneous, intramuscular, and intra-peritoneal.

For prevention of surgical adhesions, the tribonectins described herein are administered in the form of gel, foam, fiber or fabric. A tribonectin formulated in such a manner is placed over and between damaged or exposed tissue interfaces in order to prevent adhesion formation between apposing surfaces. To be effective, the gel or film must remain in place and prevent tissue contact for a long enough time so that when the gel finally disperses and the tissues do come into contact, they will no longer have a tendency to adhere. Tribonectins formulated for inhibition or prevention of adhesion formation (e.g, in the form of a membrane, fabric, foam, or gel) are evaluated for prevention of post-surgical adhesions in a rat cecal abrasion model (Goldberg et al., In Gynecologic Surgery and Adhesion Prevention. Willey-Liss, pp. 191–204, 1993). Compositions are placed around surgically abraded rat ceca, and compared to non-treated controls (animals whose ceca were abraded but did not receive any treatment). A reduction in the amount of adhesion formation in the rat model in the presence of the tribonectin formulation compared to the amount in the absence of the formulation indicates that the formulation is clinically effective to reduce tissue adhesion formation.

Tribonectins are also used to coat artificial limbs and joints prior to implantation into a mammal. For example, such devices are dipped or bathed in a solution of a tribonectin, e.g, as described in U.S. Pat. Nos. 5,709,020 or 5,702,456.

Lubricating polypeptides are at least about 10 amino acids ((containing at least one KEPAPTT (SEQ ID NO:3)) or XXTTTX (SEQ ID NO:4) repeat), usually about 20 contiguous amino acids, preferably at least 40 contiguous amino acids, more preferably at least 50 contiguous amino acids, and most preferably at least about 60 to 80 contiguous amino acids in length. For example, the polypeptide is approximately 500 amino acids in length and contains 76 repeats of KEPAPTT (SEQ ID NO:3). The polypeptide is less than 1404 residues in length, e.g., it has the amino acid sequence of naturally-occurring MSF (SEQ ID NO:1) but lacks at least 5, 10, 15, 20, or 24 amino acids at the N-terminus of naturally-occurring MSF. Such peptides are generated by methods known to those skilled in the art, including proteolytic cleavage of a recombinant MSF protein, de novo synthesis, or genetic engineering, e.g., cloning and expression of at least exon 6, 7, 8, and/or 9 of the MSF gene.

Tribonectin polypeptides are also biochemically purified. The enzyme chymotrypsin cleaves at sites which bracket amino acids encoded by exon 6 of the MSF gene. Thus, a polypeptide containing amino acids encoded by exon 6 of the MSF gene (but not any other MSF exons) is prepared from a naturally-occurring or recombinantly produced MSF gene product by enzymatic digestion with chymotrypsin. The polypeptide is then subjected to standard biochemical purification methods to yield a substantially pure polypeptide suitable for therapeutic administration, evaluation of lubricating activity, or antibody production.

Therapeutic compositions are administered in a pharmaceutically acceptable carrier (e.g., physiological saline). Carriers are selected on the basis of mode and route of administration and standard pharmaceutical practice. A therapeutically effective amount of a therapeutic composition (e.g., lubricating polypeptide) is an amount which is capable of producing a medically desirable result, e.g., boundary lubrication of a mammalian joint, in a treated animal. A medically desirable result is a reduction in pain (measured, e.g., using a visual analog pain scale described in Peyron et al., 1993, J. Rheumatol. 20 (suppl.39):10–15) or increased ability to move the joint (measured, e.g., using pedometry as described in Belcher et al., 1997, J. Orthop. Trauma 11:106–109). Another method to measure lubricity of synovial fluid after treatment is to reaspirate a small volume of synovial fluid from the affected joint and test the lubricating properties in vitro using a friction apparatus as described herein.

As is well known in the medical arts, dosage for any one animal depends on many factors, including the animal's size, body surface area, age, the particular compound to be administered, sex, time and route of administration, general health, and other drugs being administered concurrently. Administration is generally local to an injured or inflamed joint. Alternatively, the polypeptides are administered via a timed-release implant placed in close proximity to a joint for slow release at the site of an injured or inflamed joint.

Gene Therapy

Gene therapy is carried out by administering to a mammal a nucleic acid encoding a therapeutic lubricating polypeptide, e.g., DNA encoding one or more repeats or the amino acid sequence KEPAPTT (SEQ ID NO:3) or DNA encoding a lubricating fragment of MSF, by standard vectors and/or gene delivery systems. Suitable gene delivery systems include liposomes, receptor-mediated delivery systems, naked DNA, and viral vectors such as herpes viruses, retroviruses, adenoviruses and adeno-associated viruses.

In addition to a gene delivery system as described above, the therapeutic composition may include a pharmaceutically acceptable carrier, e.g., a biologically compatible vehicle such as physiological saline, suitable for administration to an animal. A therapeutically effective amount of a nucleic acid or polypeptide composition is an amount which is capable of producing a medically desirable result in a treated animal, e.g., a reduction in pain associated with joint movement, an increase in lubricating function of synovial fluid.

Parenteral administration, such as intravenous, subcutaneous, intramuscular, and intraperitoneal delivery routes, may be used to deliver the compound. Preferably, therapeutic compositions such as nucleic acids or polypeptides are delivered intra-articularly. Dosage for any one patient depends upon many factors, including the patient's size, body surface area, age, the particular compound to be administered, sex, time and route of administration, general health, and other drugs (e.g., anti-inflammatory drugs, viscotherapeutic drugs) being administered concurrently. A preferred dosage for administration of nucleic acids is from approximately $10^6$ to $10^{22}$ copies of the nucleic acid molecule.

DNA is be introduced into target cells of the patient by standard vectors, e.g., a vector which contains DNA encoding a tribonectin operably linked to a promoter sequence. Suitable gene delivery systems may include liposomes, receptor-mediated delivery systems, naked DNA, and viral vectors such as herpes viruses, retroviruses, and adenoviruses, among others.

DNA may be administered locally using an adenovirus or adeno-associate virus delivery system using standard methods. For example, methods of delivering DNA intra-articularly to synovial fluid and methods of delivering DNA to cells from synovial fluid (e.g, synovial fibroblasts or chondrocytes) are described in U.S. Pat. No. 5,858,355. The only cis-acting sequences required for replication and packaging of recombinant adeno-associated virus (AAV) vector are the AAV terminal repeats. Up to 4 kb of DNA is inserted between the terminal repeats without effecting viral replication or packaging. To package a recombinant AAV vector, a plasmid containing the terminal repeats and DNA encoding a therapeutic polypeptide is co-transfected into cells with a plasmid that expresses AAV rep and capsid proteins. The transfected cells are then infected with adeno-associated virus, and recombinant AAV virus containing the desired sequences is isolated from cells approximately 48–72 hours after transfection. Recombinant virus is then administered for gene therapy applications using known methods.

Electroporation is another method of introducing DNA into target cells, e.g., synovial fibroblasts or chondrocytes, ex vivo. Cells to be electroporated are placed into Hepes buffer saline (HBS) at a concentration of about $10^7$ cells per ml. The DNA to be electroporated is added at a concentration of approximately 5–20 µg/ml of HBS. The mixture is placed into an electroporation device and an electric field is applied according to standard protocols, e.g., in a range of between about 250 and 300 volts. Following introduction of DNA into synovial cells ex vivo, the genetically modified autologous synovial cells are transplanted back into the donor by intra-articular injection. Approximately $10^7$ cells are injected intra-articularly into joints in a volume of approximately 1 ml.

Synovial cells into which DNA is introduced are obtained using routine methods, e.g., through an arthroscope. The arthroscope is a small, hollow rod inserted into the knee via a small puncture wound which allows access to a surgical instrument to recover synovial cells arthroscopically. In some cases, the synovial cells in arthroscopically excised tissue are aseptically recovered by enzymatic digestion of the connective tissue matrix. For example, the synovium is cut into pieces of approximately 1 mm diameter and digested sequentially with trypsin (0.2% w/v in Gey's Balanced Salt Solution) for 30 minutes at 37° C., and collagenase (0.2% w/v in Gey's Balanced Salt Solution) for 2 hours at 370C. A suspension of genetically-modified cells is injected into a recipient mammalian joint. Intra-articular injections of this type are routine and carried out in the doctor's office without additional surgical intervention. Repeat injections are carried out as needed.

Alternatively, the DNA (naked or packaged in a virus) is formulated in a suitable pharmaceutical carrier and injected intra-articularly. Gene therapy is also administered as a prophylactic measure to prevent the development of osteoarthritis in those individuals determined to be highly susceptible of developing this disease, e.g., those who have suffered an acute joint injury. Direct intra-articular injection of a DNA encoding a therapeutic polypeptide into a joint results in transfection of the recipient synovial cells to allow expression of DNA.

Drugs which stimulate an endogenous tribonectin promoter, e.g., TGFβ, may also be administered as described above to increase the level of synovial expression.

Production of Antibodies Specific for Synovial Lubricating Polypeptides

Antibodies specific for lubricating polypeptides are obtained by techniques well known in the art. Such antibodies can be polyclonal or monoclonal. Polyclonal antibodies can be obtained, for example, by the methods described in Ghose et al., Methods in Enzymology, Vol. 93, 326–327, 1983. For example, a lubricating polypeptide encoded by nucleotides 632–3453 of SEQ ID NO:2 is used as an immunogen to stimulate the production of polyclonal antibodies in the antisera of a rabbit. Similar methods can be used to raise antisera in animals such as goats, sheep, and rodents.

Monoclonal antibodies are obtained by the well known process described by Milstein and Kohler in Nature, 256:495–497, 1975, or as modified by Gerhard, Monoclonal Antibodies, Plenum Press, 1980, pages 370–371. Hybridomas are screened to identify those producing antibodies that are highly specific for a synovial lubricating polypeptide. Preferably, the antibody has an affinity of at least about $10^8$ liters/mole and more preferably, an affinity of at least about $10^9$ liters/mole. Monoclonal or polyclonal antibodies provide a means of rapidly purifying large quantities of recombinant lubricating polypeptides.

In addition to antibodies which are directed to the peptide core of a tribonectin, an antibody directed to a sugar portion or to a glycopeptide complex of a tribonectin is desirable. To generate an antibody to the peptide core, a peptide spanning amino acids 200–350 of SEQ ID NO:1 is used. Shorter peptides, e.g,. 8–15 amino acids in length, which are identical to an 8–15 amino acid portion of amino acids 200–350 of SEQ ID NO:1 are also used to generate such antibodies. Other peptides to be used as immunogens for antibodies specific for the peptide core of a tribonectin include those which are in the region of amino acids 24–66 of SEQ ID NO:1, amino acids 105–155 of SEQ ID NO:1, or amino acids 156–199 of SEQ ID NO:1. To generate antibodies which bind to a glycosylated tribonectin polypeptide (but not a deglycosylated or nonglycosylated form), the immunogen is preferably a glycopeptide, the amino acid sequence of which spans a highly glycosylated portion of a tribonectin, e.g, a peptide with an amino acid sequence of residues 200–1140 of SEQ ID NO:1. Shorter glycopeptides, e.g., 8–15 amino acids in length, within the same highly glycosylated region are also used as immunogens. Methods of generating antibodies to highly glycosylated biomolecules are known in the art, e.g., as described by Schneerson et al., 1980, J. Exp. Med. 152:361–376.

Methods of Diagnosis

Osteoarthritis is a disease that develops slowly and is difficult to diagnose until its late stages when joint pain often compels an individual to seek medical treatment. Early diagnosis of osteoarthritis or a predisposition to develop the disease allows early intervention to prevent or reduce the development of advanced osteoarthritis. The invention provides methods of early detection of this disease or a predisposition to develop it by testing bodily fluids such as serum or urine for the presence of fragments of naturally-occurring tribonectins or the presence of fragments of MSF. Detection and quantitation of such peptides in biological fluids is well known in the art. For example, a standard sandwich ELISA assay is carried out using two different antibodies (e.g., a first antibody which binds to an oligosaccharide portion of the glycopeptide and a second antibody which binds to the peptide core of the glycopeptide) to a naturally-occurring tribonectin. Alternatively, standard protein sequencing by liquid chromatography and mass spectroscopy, as is described below, is used to detect MSF fragments in biological samples. A control value is a predetermined value associated with a negative diagnosis; alternatively, a control sample is a biological sample from a mammal known to be free of osteoarthritis. An increase in the amount compared to a control value or sample indicates that the mammal suffers from osteoarthritis or is predisposed to developing osteoarthritis.

Characterization of a Tribonectin from Human Synovial Fluid

Aliquots of synovial fluid from patients undergoing diagnostic arthroscopy and total knee replacement were collected and assayed in the friction apparatus. In both cases, the synovial fluid was aspirated prior to initiation of any surgical procedure and immediately centrifuged at 10,000×g at 4° C. for 2 hrs to remove cellular debris. Samples which were contaminated with blood were discarded. Aliquots with normal lubricating ability were pooled and stored at −20° C.

Purification and Isolation of a Tribonectin

Human synovial fluid (200 ml) was filtered through 0.22 μm sterile filter units (Nalgene) at 4° C. over two days. Retentate was scraped off filter membranes and resuspended with 50 mM NaAc buffer, pH 5.5, to the original synovial fluid volume containing proteolytic inhibitors: 1 mM phenylmethyl sulfonyl fluoride (PMSF), 1 mM parachloromercuricbenzoic acid (PCMB), and 10 mM ethylenediamine tetraacetate (EDTA). Digestion of hyaluronic acid was carried out at 37° C. by streptomyces hyaluronidase at 1 U/ml of resuspended synovial fluid. The digest was loaded on a DEAE column (Whatman International, Maidstone, UK) settled volume of 300 ml, equilibrated with NaAc buffer, 50 mM and washed with 1.5 L of the same buffer. The material with lubricating activity was eluted off of the DEAE matrix with 1 M NaCl. A 1 L wash was collected and concentrated via a 500 ml Amicon flow cell with an XM-100 membrane (mw cutoff 100 kDa). The concentrated sample was dialyzed against 25 mM phosphate buffer, pH 7.4, containing 0.15 M NaCl and 0.5 mM $CaCl_2$.

The DEAE-bound concentrate was loaded onto a peanut agglutinin (PNA)-agarose affinity column with a settled bed volume of 25 ml, equilibrated at room temperature with 25 mM phosphate and 0.15 NaCl buffer, pH 7.4. Unbound protein was eluted with the same buffer until absorbance at 230 and 280 nm decreased to background. Material with lubricating activity was maximally eluted in the presence of a step-wise gradient of α-lactose at a concentration of 0.07 M in 25 mM Tris and 0.15 M NaCl at pH 7.4. This material was loaded onto an Actigel ALD agarose (Sterogene Bioseparations, Arcadia, Calif.) coupled via amine groups to a murine monoclonal antibody against human fibronectin (Zymed Laboratories Inc., San Francisco, Calif.) to remove fibronectin as a contaminant. Eluted material was assayed for purity on SDS-PAGE (5–15% acrylamide) stained with Coomassie blue and by HPLC.

Protein electrophoresis standards were from GibcoBRL (Grand Island, N.Y.), and DNA ladder standard was from FMC Bioproducts (Rockland, Me.).

High Pressure Liquid Chromatography

A μBondpak C18 3.9×150 mm column (Waters, Milford, Mass.) was eluted in reverse phase with 45% (v/v) methanol (Sigma) and 5% (v/v) acetonitrile (Aldrich) HPLC grade at 1 ml/min at 350C. The eluate was assayed by a photo diode array detector PDA 996 (Waters), and material in peak fractions were analyzed by purity plots calculated using Millenium 32 software (Waters).

Friction Apparatus

A standard friction apparatus (e.g., an apparatus described by Jay et al., 1992, Conn. Tiss. Res. 28:71–88 or Jay et al., 1998, J. Biomed. Mater. Res. 40:414–418). Natural latex was oscillated against a ring of polished glass with a constant contact area of 1.59 $cm^2$. The bearing system was axially loaded within a gimbals system free to rotate around two perpendicular horizontal axes. Latex and glass as bearing materials were chosen because they offer a flat surface with small asperity heights on the order of 0.05 mm. Latex, like cartilage, is compliant. Within the gimbals system, these surfaces possess near perfect co-planarity. Accordingly, fluid wedges were not generated and only a thin layer of boundary fluid was present. The entraining velocity (i.e., sliding speed) was 0.37 mm/sec with a constant contact pressure of 0.35×106 $N/m^2$.

The friction apparatus recorded displacements of the gimbals system around the vertical loading axis through a linear displacement voltage transducer, the output voltage of which was directly proportional to the magnitude of the frictional torque. The peak to peak amplitude of this signal was related to $\mu$ by a previous calibration with known frictional torque.

Test surfaces were cleaned extensively before use. A 3.8×3.8 cm piece of latex strapped onto the stainless steel stud was washed under running distilled deionized water (DDW) for 2 min. It was then placed in a shallow bath of 0.9% NaCl physiological saline (PS). The glass slide was scrubbed with a 1% (v/v) 7× detergent (Flow Laboratories, McLean, Va.) solution in DDW for 10 min and then allowed to soak in the same solution at 100° C. A 5 min. scrubbing was also performed with the hot 7× solution followed by rinsing for 2–4 min. under running DDW.

The $\mu$ was measured at 35° C. and was preceded by a baseline measurement of the $\mu$ with PS. Lubrication was manifested by a reduction of $\mu$ relative to the $\mu$ of PS. Negative delta $\mu$ values indicate lubrication, whereas positive values indicate friction. Addition of 200 μl of PS and later 200 μl of test lubricant was followed by bringing the bearing surfaces close enough so that the solution wet both surfaces. After 5 min for equilibration, the latex-coated bearing was brought to rest on the glass as it was oscillating. Peak to peak voltages were automatically recorded after 1, 3 and 5 mins. At this point, the surfaces were separated for 2 min. and then brought back together for another 5 min session. The 3 and 5 min. $\mu$ values of the last two 5 min. sessions typically stabilized and were recorded.

Human serum fibronectin was purchased from Sigma Chemical (F0895, St. Louis, Mo.) and dialyzed against PS before use in the friction apparatus.

Boundary lubricants exert their effect by changing the physico-chemical characteristics of a surface. Bearing surfaces must generate a mutual repulsion in order to be lubricated in the boundary mode. Typical room temperature examples of boundary lubricants are graphite, teflon and molybdenum sulphide. Such compositions reduce friction between bearing surfaces, and therefore, are used as positive controls in assay to measure the lubricating properties of tribonectins. Tribonectins are boundary lubricants that can have an amphipathic character by coating non-biologic hydrophobic surfaces such as latex. The oligosaccharide component of a tribonectin networks with the surrounding aqueous environment. When the ultimate and penultimate sugars are removed from a naturally-occurring tribonectin purified from synovial fluid, the lubricating ability is eliminated.

The latex:glass arthrotripsometer offers an expedient way to test purified biological lubricating factors repetitively with reproducibility. Natural latex and polished glass represent bearing surfaces with little if any variation in physico-chemical characteristic from test to test. By contrast, resected cartilage apposed to either polished glass or cartilage itself will experience deformation that cannot be accurately controlled. The $\mu$ observed in a cartilage-cartilage bearing lubricated by synovial fluid was between 0.005 and 0.024. The values of $\mu$ in the latex:glass system were appreciably higher and typically 0.04 or less. Differences in $\mu$ between the bearing materials are attributed to the 80% (w/w) water content of cartilage.

Protein Sequencing by Liquid Chromatography and Mass Spectrometry (LCMS)

Standard LCMS was carried out on tryptic digests of the purified lubricating material described above. Excised bands from 2 mm thick 5–20% gradient SDS-PAGE gels (Bio-rad Laboratories, Hercules, Calif.) containing the lubricating material was analyzed. The material was deglycosylated by NaNase III and O-glycosidase DS (Glyko, Novato, Calif.). Deglycosylation was carried out with the above enzymes at activities of 0.17 U/ml and 0.10 U/ml, respectively, for 18 hrs in the presence of 0.5 mg/ml of a tribonectin purified from synovial fluid. In all cases, the gel slices were cut through the middle of the band and were 16 mm$^3$ in size. All contact surfaces were carefully cleaned with 50% (v/v) acetonitrile. Sequence data was entered into the BLAST GENBANK® search algorithm and matches identified.

Isolation and Culture of Human Synovial Fibroblasts

Human synovium with a normal appearance was obtained from a 30 year old white male undergoing arthroscopy. Within 1 hr after surgery, the synovial tissue explant was washed three times with Dulbecco's calcium- and magnesium-free phosphate-buffered saline (GIBCO). Pieces 2 mm$^3$ in size were placed in Dulbecco's modification of Eagle's medium (GIBCO), supplemented with 100 U of penicillin and 100 µg of streptomycin per ml (GIBCO), containing 4 mg/ml of Clostridiopeptidase A (Worthington Biochemical CLS, 125–200 U/mg) sterilized through a 0.22 µm filter (Nalge). The tissue fragments were further divided with scissors in a 100 mm plastic petri dish (Falcon) and incubated for 4 hrs in 20 ml of medium at 37° C. in a moist atmosphere of 5% carbon dioxide and 95% air.

The digest was well mixed many times by aspiration into and expulsion from a Pasteur pipette. An equal volume of 0.05% trypsin and 0.02% EDTA in modified Puck's Saline A (GIBCO) were added and incubation continued for a further hour under the same conditions. The suspension was centrifuged 10 min at 400×g at 23° C. and washed three times each with 40 ml of calcium- and magnesium-free phosphate-buffered saline. The pellet was suspended in modified Eagle's medium (20 ml) supplemented with 10% fetal bovine serum (Flow Laboratories), 100 U of penicillin, and 100 mg of streptomycin per ml. Two milliliters of this final mixture were plated per 60 mm plastic petri dish (Falcon). Synovial fibroblasts were grown to confluence and cells harvested. Human skin fibroblasts (American Type Culture Collection (ATCC) Designation CCD-1099SK; ATCC, Mannassas, Va.) which served as a control were also grown and harvested using the above procedure.

RNA Extraction and RT-PCR Analyses

RNA from synovial and skin fibroblasts was purified by RNeasy mini-columns and reagents (Qiagen, Crawley, Ltd., UK). Contaminating genomic DNA was removed by DNAshredder and DNase (RNase free) (Qiagen). First strand cDNA was synthesized by reverse transcription and PCR amplification using the following oligonucleotide primers. MSF-exon 6 forward primer 5'-CCAAACCACCAGTTGTAGATGAAGC-3', (SEQ ID NO:15) and MSF-exon 6 reverse primer 5'-GCGGAAGTAGTCTTCTCTTTTCCATCAG-3' (SEQ ID NO:16). These primers correspond to nucleotide position numbers 674–698 and 953–926, respectively, of the human MSF gene (SEQ ID NO:2; GENBANKO accession number U70136). Thermal cycling conditions were 42° C. for 12 mins., 95° C. for 10 mins., followed by 43 cycles between 94° C.×20 secs and 55–65° C.×30–90 secs. A final extension for 7 mins was at 72° C. (Perkin Elmer Biosystems).

Alternative Splice Variant of MSF is a Tribonectin

A lubricating polypeptide was purified from human synovial fluid using standard biochemical methods followed by affinity chromatography with peanut agglutinin. The final fraction, which solely possessed lubricating ability, contained a product with an apparent molecular weight of 280 kDa. Components with a molecular weight in excess of 280 kDa were not observed. LCMS performed on tryptic fragments from the 280 kDa excised band indicated the presence of two different proteins that matched in the BLAST search algorithm to fibronectin precursor and MSF (GenBank Accession No. U70136). Sequences of MSF were identified from both native and deglycosylated lubricating polypeptides. Accordingly, the purification scheme was terminated with an anti-fibronectin column resulting in the elimination of fibronectin as an impurity (as assayed by C18 analytical HPLC and purity plot analysis). In addition, lower molecular weight bands at 70 and 160 kDa on SDS-PAGE were absent from the purified tribonectin preparation eluting from the anti-fibronectin column. The purified tribonectin assayed in the friction apparatus was found to display boundary lubricating activity similar to that of whole synovial fluid (Table 5). By contrast, purified serum fibronectin raised friction indicating that synovial fluid lubricating ability was mediated by the purified tribonectin.

TABLE 5

Friction coefficients for a tribonectin purified from human synovial fluid and fibronectin (Mean + SD; N = 3)

| LUBRICANT* | µ | µ (PS**) | Δµ |
|---|---|---|---|
| Tribonectin | 0.047 ± .006 | 0.131 + .007 | −0.084 ± .004 |
| HSF† | 0.040 ± .005 | 0.135 + .009 | −0.095 ± .011 |
| Fibronectin | 0.181 | 0.136 | +0.045 ± .005 |

*Tested at a concentration of 250 µg/ml in PS.
**Physiological saline.
†Post-mortem human synovial fluid Furthermore, LCMS of tryptic fragments identified portions of exons 6 through 9 of MSF, inclusively. Purified tribonectin reacted to peanut agglutinin indicating the presence of β(1–3)Gal-GalNAC oligosaccharides by virtue of its purification. An increase in electrophoretic mobility was observed after digestion with NaNase III and O-glycosidase DS, indicating that the purified tribonectin is highly glycosylated via O-linked oligosaccharides. The apparent molecular weight of deglycosylated tribonectin purified from synovial fluid was 120 kDa.

RT-PCR analysis was completed using primers specific for nucleotide sequences encoding the N-terminal end of exon 6 of MSF. RT-PCR's using human synovial fibroblast RNA generated a 280 bp product, the predicted distance between the designed primers. Similar experiments without reverse transcriptase did not generate this product indicating that the RNA was free of genomic DNA. Purified RNA from skin fibroblasts did not produce any product using the same primers.

MSF was first isolated from human monocytes; a 25 kDa fragment of MSF was found to stimulate the development of megakaryocytes. MSF precursor protein is 1404 residues in size and constructed from 12 exons. Exon 6 appears to encodes a centrally located mucin that is 940 residues in length. Exon 6 has homology to vitronectin, exons 2 and 3 appear homologous to somatomedin B-like regions, and exons 8,9 are similar to hemopexin-like regions in vitronectin. Hemopexin is a serum heme scavenging protein that interacts with hyaluronate.

A tribonectin purified from synovial fluid and an articular cartilage superficial zone protein (SZP) purified from articular cartilage share sequence identity with MSF but differ in their apparent molecular weights and amino acid sequences.

Other embodiments are within the following claims.

---

What is claimed is:

1. A method of lubricating a mammalian joint, comprising contacting said joint with a purified polypeptide comprising residues 200–1140 of SEQ ID NO:1 and an O-linked oligosaccharide.

2. The method of claim 1, wherein said joint is an articulating joint of a human.

3. The method of claim 1, wherein said joint is an articulating joint of a dog.

4. The method of claim 1, wherein said joint is an articulating joint of a horse.

5. The method of claim 1, wherein said tribonectin is administered intra-articularly.

6. A method of inhibiting adhesion formation between a first surface and a second surface in a mammal, said method comprising placing a tribonectin between said first and second surfaces in an amount sufficient to prevent adhesion of said surfaces in said mammal, wherein said tribonectin is a purified polypeptide comprising residues 200–1140 of SEQ ID NO:1 and an O-linked oligosaccharide.

7. The method of claim 6, wherein said first surface and said second surface are both injured tissues of said mammal.

8. The method of claim 6, wherein said first or said second surface is an artificial device.

9. The method of claim 8, wherein said artificial device is an orthopedic implant.

10. The method of claim 6, wherein said tribonectin is present in a composition, said composition being in the form of a membrane, foam, gel, or fiber.

11. The method of claim 6, wherein said first and said second surfaces are tissues injured due to a surgical incision.

12. The method of claim 6, wherein said first and said second surfaces are tissues injured due to trauma.

13. A method of lubricating a mammalian joint, comprising contacting said joint with a purified tribonectin, wherein said tribonectin is a fragment of megakaryocyte stimulating factor (MSF) comprising residues 200–1140 of SEQ ID NO: 1, wherein said fragment comprises an O-linked oligosaccharide.

14. The method of claim 13, wherein said tribonectin further comprises residues 1141–1167 of SEQ ID NO:1.

15. The method of claim 14, wherein said tribonectin further comprises residues 1168–1212 of SEQ ID NO: 1.

16. The method of claim 15, wherein said tribonectin further comprises residues 1213–1263 of SEQ ID NO: 1.

17. The method of claim 13, wherein said tribonectin comprises residues 200–1263 of SEQ ID NO: 1.

18. The method of claim 1, wherein said polypeptide is recombinant.

19. The method of claim 6, wherein said polypeptide is recombinant.

20. The method of claim 1, wherein said polypeptide is chemically synthesized.

21. The method of claim 6, wherein said polypeptide is chemically synthesized.

22. The method of claim 1, 6, or 13, wherein said O-linked oligosaccharide is β(1,3)Gal-GalNAC.

23. The method of claim 1, 6, or 13, wherein said O-linked oligosaccharide is β(1,3)Gal-GalNeuAc.

24. A method of lubricating a mammalian joint, comprising contacting said joint with a purified polypeptide comprising an amino acid sequence in which at least one threonine in the amino acid sequence of residues 200–1140 of SEQ ID NO:1 is substituted with a serine, wherein said polypeptide is glycosylated.

25. The method of claim 24, wherein said polypeptide comprises an O-linked oligosaccharide.

26. A method of lubricating a mammalian joint, comprising contacting said joint with a purified tribonectin, wherein said tribonectin is an alternatively spliced variant of human megakaryocyte stimulating factor (MSF) gene, wherein said variant comprises at least an O-glycosylated mucin domain, wherein said mucin domain is encoded by exon 6 of a human MSF gene.

* * * * *

SEQUENCE LISTING

<160> NUMBER OF SEQ ID NOS: 16

<210> SEQ ID NO 1
<211> LENGTH: 1404
<212> TYPE: PRT
<213> ORGANISM: Homo sapiens

<400> SEQUENCE: 1

```
Met Ala Trp Lys Thr Leu Pro Ile Tyr Leu Leu Leu Leu Leu Ser Val
 1               5                  10                  15

Phe Val Ile Gln Gln Val Ser Ser Gln Asp Leu Ser Ser Cys Ala Gly
            20                  25                  30

Arg Cys Gly Glu Gly Tyr Ser Arg Asp Ala Thr Cys Asn Cys Asp Tyr
        35                  40                  45

Asn Cys Gln His Tyr Met Glu Cys Cys Pro Asp Phe Lys Arg Val Cys
    50                  55                  60

Thr Ala Glu Leu Ser Cys Lys Gly Arg Cys Phe Glu Ser Phe Glu Arg
65                  70                  75                  80

Gly Arg Glu Cys Asp Cys Asp Ala Gln Cys Lys Lys Tyr Asp Lys Cys
                85                  90                  95

Cys Pro Asp Tyr Glu Ser Phe Cys Ala Glu Val His Asn Pro Thr Ser
            100                 105                 110

Pro Pro Ser Ser Lys Lys Ala Pro Pro Pro Ser Gly Ala Ser Gln Thr
        115                 120                 125

Ile Lys Ser Thr Thr Lys Arg Ser Pro Lys Pro Pro Asn Lys Lys Lys
    130                 135                 140

Thr Lys Lys Val Ile Glu Ser Glu Glu Ile Thr Glu Glu His Ser Val
145                 150                 155                 160

Ser Glu Asn Gln Glu Ser Ser Ser Ser Ser Ser Ser Ser Ser Ser Ser
                165                 170                 175

Ser Thr Ile Trp Lys Ile Lys Ser Ser Lys Asn Ser Ala Ala Asn Arg
            180                 185                 190

Glu Leu Gln Lys Lys Leu Lys Val Lys Asp Asn Lys Lys Asn Arg Thr
        195                 200                 205

Lys Lys Lys Pro Thr Pro Lys Pro Pro Val Val Asp Glu Ala Gly Ser
    210                 215                 220

Gly Leu Asp Asn Gly Asp Phe Lys Val Thr Thr Pro Asp Thr Ser Thr
225                 230                 235                 240

Thr Gln His Asn Lys Val Ser Thr Ser Pro Lys Ile Thr Thr Ala Lys
                245                 250                 255

Pro Ile Asn Pro Arg Pro Ser Leu Pro Pro Asn Ser Asp Thr Ser Lys
            260                 265                 270

Glu Thr Ser Leu Thr Val Asn Lys Glu Thr Thr Val Glu Thr Lys Glu
        275                 280                 285

Thr Thr Thr Thr Asn Lys Gln Thr Ser Thr Asp Gly Lys Glu Lys Thr
    290                 295                 300

Thr Ser Ala Lys Glu Thr Gln Ser Ile Glu Lys Thr Ser Ala Lys Asp
305                 310                 315                 320
```

-continued

```
Leu Ala Pro Thr Ser Lys Val Leu Ala Lys Pro Thr Pro Lys Ala Glu
            325                 330                 335

Thr Thr Thr Lys Gly Pro Ala Leu Thr Thr Pro Lys Glu Pro Thr Pro
            340                 345                 350

Thr Thr Pro Lys Glu Pro Ala Ser Thr Thr Pro Lys Glu Pro Thr Pro
            355                 360                 365

Thr Thr Ile Lys Ser Ala Pro Thr Thr Pro Lys Glu Pro Ala Pro Thr
            370                 375                 380

Thr Thr Lys Ser Ala Pro Thr Thr Pro Lys Glu Pro Ala Pro Thr Thr
385                 390                 395                 400

Thr Lys Glu Pro Ala Pro Thr Thr Pro Lys Glu Pro Ala Pro Thr Thr
            405                 410                 415

Thr Lys Glu Pro Ala Pro Thr Thr Thr Lys Ser Ala Pro Thr Thr Pro
            420                 425                 430

Lys Glu Pro Ala Pro Thr Thr Pro Lys Lys Pro Ala Pro Thr Thr Pro
            435                 440                 445

Lys Glu Pro Ala Pro Thr Thr Pro Lys Glu Pro Thr Pro Thr Thr Pro
            450                 455                 460

Lys Glu Pro Ala Pro Thr Thr Lys Glu Pro Ala Pro Thr Thr Pro Lys
465                 470                 475                 480

Glu Pro Ala Pro Thr Ala Pro Lys Lys Pro Ala Pro Thr Thr Pro Lys
            485                 490                 495

Glu Pro Ala Pro Thr Thr Pro Lys Glu Pro Ala Pro Thr Thr Thr Lys
            500                 505                 510

Glu Pro Ser Pro Thr Thr Pro Lys Glu Pro Ala Pro Thr Thr Thr Lys
            515                 520                 525

Ser Ala Pro Thr Thr Thr Lys Glu Pro Ala Pro Thr Thr Thr Lys Ser
            530                 535                 540

Ala Pro Thr Thr Pro Lys Glu Pro Ser Pro Thr Thr Thr Lys Glu Pro
545                 550                 555                 560

Ala Pro Thr Thr Pro Lys Glu Pro Ala Pro Thr Thr Pro Lys Lys Pro
            565                 570                 575

Ala Pro Thr Thr Pro Lys Glu Pro Ala Pro Thr Thr Pro Lys Glu Pro
            580                 585                 590

Ala Pro Thr Thr Lys Lys Pro Ala Pro Thr Ala Pro Lys Glu Pro
            595                 600                 605

Ala Pro Thr Thr Pro Lys Glu Thr Ala Pro Thr Thr Pro Lys Lys Leu
            610                 615                 620

Thr Pro Thr Thr Pro Glu Lys Leu Ala Pro Thr Thr Pro Glu Lys Pro
625                 630                 635                 640

Ala Pro Thr Thr Pro Glu Glu Leu Ala Pro Thr Thr Pro Glu Glu Pro
            645                 650                 655

Thr Pro Thr Thr Pro Glu Glu Pro Ala Pro Thr Thr Pro Lys Ala Ala
            660                 665                 670

Ala Pro Asn Thr Pro Lys Glu Pro Ala Pro Thr Thr Pro Lys Glu Pro
            675                 680                 685

Ala Pro Thr Thr Pro Lys Glu Pro Ala Pro Thr Thr Pro Lys Glu Thr
            690                 695                 700

Ala Pro Thr Thr Pro Lys Gly Thr Ala Pro Thr Thr Leu Lys Glu Pro
705                 710                 715                 720

Ala Pro Thr Thr Pro Lys Lys Pro Ala Pro Lys Glu Leu Ala Pro Thr
            725                 730                 735

Thr Thr Lys Glu Pro Thr Ser Thr Thr Ser Asp Lys Pro Ala Pro Thr
```

-continued

```
                740                 745                 750
Thr Pro Lys Gly Thr Ala Pro Thr Thr Pro Lys Glu Pro Ala Pro Thr
            755                 760                 765
Thr Pro Lys Glu Pro Ala Pro Thr Thr Pro Lys Gly Thr Ala Pro Thr
770                 775                 780
Thr Leu Lys Glu Pro Ala Pro Thr Thr Pro Lys Lys Pro Ala Pro Lys
785                 790                 795                 800
Glu Leu Ala Pro Thr Thr Lys Gly Pro Thr Ser Thr Thr Ser Asp
                805                 810                 815
Lys Pro Ala Pro Thr Thr Pro Lys Glu Thr Ala Pro Thr Thr Pro Lys
            820                 825                 830
Glu Pro Ala Pro Thr Thr Pro Lys Lys Pro Ala Pro Thr Thr Pro Glu
            835                 840                 845
Thr Pro Pro Pro Thr Thr Ser Glu Val Ser Thr Pro Thr Thr Thr Lys
            850                 855                 860
Glu Pro Thr Thr Ile His Lys Ser Pro Asp Glu Ser Thr Pro Glu Leu
865                 870                 875                 880
Ser Ala Glu Pro Thr Pro Lys Ala Leu Glu Asn Ser Pro Lys Glu Pro
                885                 890                 895
Gly Val Pro Thr Thr Lys Thr Pro Ala Ala Thr Lys Pro Glu Met Thr
                900                 905                 910
Thr Thr Ala Lys Asp Lys Thr Thr Glu Arg Asp Leu Arg Thr Thr Pro
            915                 920                 925
Glu Thr Thr Ala Ala Pro Lys Met Thr Lys Glu Thr Ala Thr Thr
930                 935                 940
Thr Glu Lys Thr Thr Glu Ser Lys Ile Thr Ala Thr Thr Thr Gln Val
945                 950                 955                 960
Thr Ser Thr Thr Thr Gln Asp Thr Thr Pro Phe Lys Ile Thr Thr Leu
                965                 970                 975
Lys Thr Thr Thr Leu Ala Pro Lys Val Thr Thr Thr Lys Lys Thr Ile
                980                 985                 990
Thr Thr Thr Glu Ile Met Asn Lys Pro Glu Glu Thr Ala Lys Pro Lys
            995                 1000                1005
Asp Arg Ala Thr Asn Ser Lys Ala Thr Thr Pro Lys Pro Gln Lys Pro
    1010                1015                1020
Thr Lys Ala Pro Lys Lys Pro Thr Ser Thr Lys Lys Pro Lys Thr Met
1025                1030                1035                1040
Pro Arg Val Arg Lys Pro Lys Thr Thr Pro Thr Pro Arg Lys Met Thr
                1045                1050                1055
Ser Thr Met Pro Glu Leu Asn Pro Thr Ser Arg Ile Ala Glu Ala Met
            1060                1065                1070
Leu Gln Thr Thr Thr Arg Pro Asn Gln Thr Pro Asn Ser Lys Leu Val
            1075                1080                1085
Glu Val Asn Pro Lys Ser Glu Asp Ala Gly Gly Ala Glu Gly Glu Thr
    1090                1095                1100
Pro His Met Leu Leu Arg Pro His Val Phe Met Pro Glu Val Thr Pro
1105                1110                1115                1120
Asp Met Asp Tyr Leu Pro Arg Val Pro Asn Gln Gly Ile Ile Ile Asn
                1125                1130                1135
Pro Met Leu Ser Asp Glu Thr Asn Ile Cys Asn Gly Lys Pro Val Asp
                1140                1145                1150
Gly Leu Thr Thr Leu Arg Asn Gly Thr Leu Val Ala Phe Arg Gly His
                1155                1160                1165
```

Tyr Phe Trp Met Leu Ser Pro Phe Ser Pro Ser Pro Ala Arg Arg
         1170                1175                1180

Ile Thr Glu Val Trp Gly Ile Pro Ser Pro Ile Asp Thr Val Phe Thr
1185                1190                1195                1200

Arg Cys Asn Cys Glu Gly Lys Thr Phe Phe Lys Asp Ser Gln Tyr
         1205                1210                1215

Trp Arg Phe Thr Asn Asp Ile Lys Asp Ala Gly Tyr Pro Lys Pro Ile
         1220                1225                1230

Phe Lys Gly Phe Gly Leu Thr Gly Gln Ile Val Ala Ala Leu Ser
         1235                1240                1245

Thr Ala Lys Tyr Lys Asn Trp Pro Glu Ser Val Tyr Phe Lys Arg
         1250                1255                1260

Gly Gly Ser Ile Gln Gln Tyr Ile Tyr Lys Gln Glu Pro Val Gln Lys
1265                1270                1275                1280

Cys Pro Gly Arg Arg Pro Ala Leu Asn Tyr Pro Val Tyr Gly Glu Met
         1285                1290                1295

Thr Gln Val Arg Arg Arg Phe Glu Arg Ala Ile Gly Pro Ser Gln
         1300                1305                1310

Thr His Thr Ile Arg Ile Gln Tyr Ser Pro Ala Arg Leu Ala Tyr Gln
         1315                1320                1325

Asp Lys Gly Val Leu His Asn Glu Val Lys Val Ser Ile Leu Trp Arg
         1330                1335                1340

Gly Leu Pro Asn Val Val Thr Ser Ala Ile Ser Leu Pro Asn Ile Arg
1345                1350                1355                1360

Lys Pro Asp Gly Tyr Asp Tyr Tyr Ala Phe Ser Lys Asp Gln Tyr Tyr
         1365                1370                1375

Asn Ile Asp Val Pro Ser Arg Thr Ala Arg Ala Ile Thr Thr Arg Ser
         1380                1385                1390

Gly Gln Thr Leu Ser Lys Val Trp Tyr Asn Cys Pro
         1395                1400

<210> SEQ ID NO 2
<211> LENGTH: 5041
<212> TYPE: DNA
<213> ORGANISM: Homo sapiens

<400> SEQUENCE: 2
gcggccgcga ctattcggta cctgaaaaca acgatggcat ggaaaacact tcccatttac      60
ctgttgttgc tgctgtctgt tttcgtgatt cagcaagttt catctcaaga tttatcaagc     120
tgtgcaggga gatgtgggga agggtattct agagatgcca cctgcaactg tgattataac     180
tgtcaacact acatggagtg ctgccctgat ttcaagagag tctgcactgc ggagctttcc     240
tgtaaaggcc gctgctttga gtccttcgag agagggaggg agtgtgactg cgacgcccaa     300
tgtaagaagt atgacaagtg ctgtcccgat tatgagagtt tctgtgcaga agtgcataat     360
cccacatcac caccatcttc aaagaaagca cctccacctt caggagcatc tcaaaccatc     420
aaatcaacaa ccaaacgttc acccaaacca ccaaacaaga agaagactaa gaaagttata     480
gaatcagagg aaataacaga gaacattct gtttctgaaa atcaagagtc ctcctcctcc      540
tcctcctctt cctcttcttc ttcaacaatt tggaaaatca gtcttccaa aaattcagct      600 gctaatagag aattacagaa gaaactcaaa gtaaaagata caagaagaa cagaactaaa     660 aagaaaccta cccccaaacc accagttgta gatgaagctg gaagtggatt ggacaatggt     720
gacttcaagg tcacaactcc tgacacgtct accacccaac acaataaagt cagcacatct     780

```
cccaagatca caacagcaaa accaataaat cccagaccca gtcttccacc taattctgat    840
acatctaaag agacgtcttt gacagtgaat aaagagacaa cagttgaaac taaagaaact    900
actacaacaa ataaacagac ttcaactgat ggaaaagaga agactacttc cgctaaagag    960
acacaaagta tagagaaaac atctgctaaa gatttagcac ccacatctaa agtgctggct   1020
aaacctacac ccaaagctga aactacaacc aaaggccctg ctctcaccac tcccaaggag   1080
cccacgccca ccactcccaa ggagcctgca tctaccacac ccaaagagcc cacacctacc   1140
accatcaagt ctgcacccac caccccaag gagcctgcac ccaccaccac caagtctgca   1200
cccaccactc ccaaggagcc tgcacccacc accaccaagg agcctgcacc caccactccc   1260
aaggagcctg cacccaccac caccaaggag cctgcaccca ccaccaagtc tgcacccc    1320 accactccca aggagcctgc acccaccacc ccaagaagc ctgccccaac tacccccaag   1380
gagcctgcac ccaccactcc caaggagcct acacccacca ctcccaagga gcctgcaccc   1440
accaccaagg agcctgcacc caccactccc aaagagcctg cacccactgc ccccaagaag   1500
cctgccccaa ctaccccaa ggagcctgca cccaccactc caaggagcc tgcacccacc   1560 accaccaagg agccttcacc caccactccc aaggagcctg cacccaccac caccaagtct   1620
gcacccacca ctaccaagga gcctgcaccc accactacca agtctgcacc caccactccc   1680
aaggagcctt cacccaccac caccaaggag cctgcaccca ccactccaa ggagcctgca   1740 cccaccaccc ccaagaagcc tgccccaact accccaaggg agcctgcacc caccactccc   1800
aaggaacctg cacccaccac caccaagaag cctgcaccca ccgctcccaa agagcctgcc   1860
ccaactaccc ccaaggagac tgcacccacc accccaagaa gctcacgcc caccaccccc   1920 gagaagctcg cacccaccac ccctgagaag cccgcaccca caccctgag gagctcgca   1980 cccaccaccc ctgaggagcc cacacccacc ccctgaggag cctgctcc caccactccc   2040 aaggcagcgg ctcccaacac ccctaaggag cctgctccaa ctacccctaa ggagcctgct   2100
ccaactaccc ctaaggagcc tgctccaact accctaagg agactgctcc aactacccct   2160
aaagggactg ctccaactac cctcaaggaa cctgcaccca ctactcccaa gaagcctgcc   2220
cccaaggagc ttgcacccac caccaccaag gagcccacat ccaccctct gacaagccc   2280 gctccaacta cccctaaggg gactgctcca actacccta aggagcctgc tccaactacc   2340
cctaaggagc tgctccaac taccctaag gggactgctc caactaccct caaggaacct   2400
gcacccacta ctcccaagaa gcctgcccc aaggagcttg cacccaccac caccaagggg   2460
cccacatcca ccactctga caagcctgct ccaactacac ctaaggagac tgctccaact   2520 accccaagg agcctgcacc cactaccccc aagaagcctg ctccaactac tcctgagaca   2580
cctcctccaa ccacttcaga ggtctctact ccaactacca ccaaggagcc taccactatc   2640
cacaaaagcc ctgatgaatc aactcctgag ctttctgcag aacccacacc aaaagctctt   2700
gaaaacagtc ccaaggaacc tggtgtacct acaactaaga ctcctgcagc gactaaacct   2760
gaaatgacta caacagctaa agacaagaca acagaaaagag acttacgtac tacacctgaa   2820
actacaactg ctgcacctaa gatgacaaaa gagacagcaa ctacaacaga aaaaactacc   2880
gaatccaaaa taacagctac aaccacacaa gtaacatcta ccacaactca agataccaca   2940
ccattcaaaa ttactactct taaaacaact actcttgcac ccaaagtaac tacaacaaaa   3000
aagacaatta ctaccactga gattatgaac aaacctgaag aaacagctaa accaaaagac   3060
agagctacta attctaaagc gacaactcct aaacctcaaa agccaaccaa agcacccaaa   3120
```

-continued

```
aaacccactt ctaccaaaaa gccaaaaaca atgcctagag tgagaaaacc aaagacgaca    3180
ccaactcccc gcaagatgac atcaacaatg ccagaattga accctacctc aagaatagca    3240
gaagccatgc tccaaaccac caccagacct aaccaaactc caaactccaa actagttgaa    3300
gtaaatccaa agagtgaaga tgcaggtggt gctgaaggag aaacacctca tatgcttctc    3360
aggccccatg tgttcatgcc tgaagttact cccgacatgg attacttacc gagagtaccc    3420
aatcaaggca ttatcatcaa tcccatgctt ccgatgaga ccaatatatg caatggtaag    3480
ccagtagatg gactgactac tttgcgcaat gggacattag ttgcattccg aggtcattat    3540
ttctggatgc taagtccatt cagtccacca tctccagctc gcagaattac tgaagtttgg    3600
ggtattcctt cccccattga tactgttttt actaggtgca actgtgaagg aaaaacttc    3660 ttctttaagg attctcagta ctggcgtttt accaatgata aaaagatgc agggtacccc    3720 aaaccaattt tcaaaggatt tggaggacta actggacaaa tagtggcagc gctttcaaca    3780
gctaaatata agaactggcc tgaatctgtg tatttttca agagaggtgg cagcattcag    3840
cagtatattt ataaacagga acctgtacag aagtgccctg gaagaaggcc tgctctaaat    3900
tatccagtgt atggagaaat gacacaggtt aggagacgtc gctttgaacg tgctatagga    3960
ccttctcaaa cacacaccat cagaattcaa tattcacctg ccagactggc ttatcaagac    4020
aaaggtgtcc ttcataatga agttaaagtg agtatactgt ggagaggact tccaaatgtg    4080
gttacctcag ctatatcact gcccaacatc agaaaacctg acggctatga ttactatgcc    4140 tttctaaag atcaatacta taacattgat gtgcctagta aacagcaag agcaattact    4200 actcgttctg ggcagacctt atccaaagtc tggtacaact gtccttagac tgatgagcaa    4260
aggaggagtc aactaatgaa gaaatgaata ataaattttg acactgaaaa acattttatt    4320
aataaagaat attgacatga gtataccagt ttatatataa aaatgttttt aaacttgaca    4380
atcattacac taaaacagat ttgataatct tattcacagt tgttattgtt tacagaccat    4440
ttaattaata tttcctctgt ttattcctcc tctccctccc attgcatggc tcacacctgt    4500
aaaagaaaaa agaatcaaat tgaatatatc ttttaagaat tcaaaactag tgtattcact    4560
taccctagtt cattataaaa aatatctagg cattgtggat ataaaactgt tgggtattct    4620
acaacttcaa tggaaattat tacaagcaga ttaatccctc ttttttgtgac acaagtacaa    4680 tctaaaagtt atattggaaa acatggaaat attaaaattt tacactttta ctagctaaaa    4740
cataatcaca aagctttatc gtgttgtata aaaaaattaa caatataatg gcaataggta    4800
gagatacaac aaatgaatat aacactataa cacttcatat ttttccaaatc ttaatttgga    4860 tttaaggaag aaatcaataa atataaata taagcacata tttattatat atctaaggta    4920
tacaaatctg tctacatgaa gtttacagat tggtaaatat cacctgctca acatgtaatt    4980
atttaataaa actttggaac attaaaaaaa taaattggag gcttaaaaaa aaaaaaaaa    5040 a                                                                   5041
```

<210> SEQ ID NO 3
<211> LENGTH: 7
<212> TYPE: PRT
<213> ORGANISM: Homo sapiens

<400> SEQUENCE: 3

Lys Glu Pro Ala Pro Thr Thr
 1               5

<210> SEQ ID NO 4

```
<211> LENGTH: 6
<212> TYPE: PRT
<213> ORGANISM: Homo sapiens
<220> FEATURE:
<221> NAME/KEY: VARIANT
<222> LOCATION: (1)...(6)
<223> OTHER INFORMATION: Xaa = Any Amino Acid

<400> SEQUENCE: 4

Xaa Xaa Thr Thr Thr Xaa
 1               5

<210> SEQ ID NO 5
<211> LENGTH: 6
<212> TYPE: PRT
<213> ORGANISM: Homo sapiens

<400> SEQUENCE: 5

Glu Pro Ala Pro Thr Thr
 1               5

<210> SEQ ID NO 6
<211> LENGTH: 6
<212> TYPE: PRT
<213> ORGANISM: Homo sapiens

<400> SEQUENCE: 6

Pro Thr Thr Lys Glu Pro
 1               5

<210> SEQ ID NO 7
<211> LENGTH: 24
<212> TYPE: DNA
<213> ORGANISM: Homo sapiens

<400> SEQUENCE: 7
agatttatca agctgtgcag ggag                                    24

<210> SEQ ID NO 8
<211> LENGTH: 22
<212> TYPE: DNA
<213> ORGANISM: Homo sapiens

<400> SEQUENCE: 8
tttacaggaa agctccgcag tg                                      22

<210> SEQ ID NO 9
<211> LENGTH: 23
<212> TYPE: DNA
<213> ORGANISM: Homo sapiens

<400> SEQUENCE: 9
tcaaggtcac aactcctgac acg                                     23

<210> SEQ ID NO 10
<211> LENGTH: 24
<212> TYPE: DNA
<213> ORGANISM: Homo sapiens

<400> SEQUENCE: 10
ctctcggtaa gtaatccatg tcgg                                    24

<210> SEQ ID NO 11
<211> LENGTH: 22
<212> TYPE: DNA
```

```
<213> ORGANISM: Homo sapiens

<400> SEQUENCE: 11
ttgttgctgc tgtctgtttt cg                                    22

<210> SEQ ID NO 12
<211> LENGTH: 24
<212> TYPE: DNA
<213> ORGANISM: Homo sapiens

<400> SEQUENCE: 12
tggataaggt ctgcccagaa cgag                                  24

<210> SEQ ID NO 13
<211> LENGTH: 23
<212> TYPE: DNA
<213> ORGANISM: Homo sapiens

<400> SEQUENCE: 13
tcaaggtcac aactcctgac acg                                   23

<210> SEQ ID NO 14
<211> LENGTH: 24
<212> TYPE: DNA
<213> ORGANISM: Homo sapiens

<400> SEQUENCE: 14
gatggtgtgt gtttgagaag gtcc                                  24

<210> SEQ ID NO 15
<211> LENGTH: 25
<212> TYPE: DNA
<213> ORGANISM: Homo sapiens

<400> SEQUENCE: 15
ccaaaccacc agttgtagat gaagc                                 25

<210> SEQ ID NO 16
<211> LENGTH: 28
<212> TYPE: DNA
<213> ORGANISM: Homo sapiens

<400> SEQUENCE: 16
gcggaagtag tcttctcttt tccatcag                              28
```